(12) United States Patent
Goud et al.

(10) Patent No.: US 7,255,741 B2
(45) Date of Patent: Aug. 14, 2007

(54) PROCESS FOR THE ISOLATION OF HIGH PURITY CRYSTALLINE CITALOPRAM BASE

(75) Inventors: Vuddamari Srinivas Goud, Karnataka (IN); Santosh Laxman Gaonkar, Mysore Karnataka (IN); Saji Thomas, Karnataka (IN); Sulur G Manjunatha, Karnataka (IN); Ashok Krishna Kulkarni, Karnataka (IN); Ambati Narahari Babu, Karnataka (IN)

(73) Assignee: Jubilant Organosys Limited (IN)

( * ) Notice: Subject to any disclaimer, the term of this patent is extended or adjusted under 35 U.S.C. 154(b) by 274 days.

(21) Appl. No.: 10/508,529

(22) PCT Filed: Mar. 21, 2003

(86) PCT No.: PCT/IB03/01641

§ 371 (c)(1),
(2), (4) Date: Jun. 10, 2005

(87) PCT Pub. No.: WO03/080590

PCT Pub. Date: Oct. 2, 2003

(65) Prior Publication Data

US 2005/0217562 A1    Oct. 6, 2005

(30) Foreign Application Priority Data

Mar. 21, 2002  (EP) ................... 02252047

(51) Int. Cl.
  *C30B 29/54*    (2006.01)

(52) U.S. Cl. ............................ 117/68; 117/70; 117/69; 117/925; 117/927

(58) Field of Classification Search .................. 117/68, 117/69, 70, 925, 927
See application file for complete search history.

(56) References Cited

U.S. PATENT DOCUMENTS

| 4,136,193 A * | 1/1979 | Bogeso et al. ............... 514/469 |
| 4,943,590 A * | 7/1990 | Boegesoe et al. ........... 514/469 |
| 2005/0165092 A1 * | 7/2005 | Petersen et al. ............ 514/469 |

* cited by examiner

*Primary Examiner*—Robert Kunemund
(74) *Attorney, Agent, or Firm*—Ostrolenk, Faber, Gerb & Soffen, LLP

(57) ABSTRACT

A method is provided for the isolation of high purity crystalline citalopram (1-[3-dimethylamino)propyl}-1-(4-fluorophenyl)-1, 3-dihydro-5-isobenzofurancarbonitrile) base directly from the alkylation reaction mixture of 5-cyanophthalane with N,N-dimethylaminoprpylchloride in a polar aprotic solvent using a strong base. The method comprises: (a) diluting the reaction mixture with ice cold water and extracting the resulting mixture with a water-immiscible organic solvent; (b) re-extracting the water-immiscible organic solvent extract with an aqueous acid; (c) diluting the aqueous acid extract with a substantially equal volume of a water miscible organic solvent, based on the volume of water in the aqueous acid extract; (d) adjusting the pH to basic with an inorganic base to precipitate free crystalline base and (e) further isolating the precipitated free crystalline base by filration.

15 Claims, No Drawings

PROCESS FOR THE ISOLATION OF HIGH PURITY CRYSTALLINE CITALOPRAM BASE

CROSS REFERENCE TO RELATED APPLICATION

This is a U.S. National stage of application No. PCT/IB03/01641, filed on 21 Mar. 2003. Priority is claimed on that application and on the following application:

Country: Europe Patent Organization, Application No. 02252047.2, Filed: 21 Mar. 2002.

This invention relates to a process for preparing citalopram (1-[3-dimethylamino)propyl]-1-(4-fluorophenyl)-1,3-dihydro-5-isobenzofurancarbonitrile), in particular to the isolation of high purity crystalline citalopram base directly from the alkylation reaction mixture of 5-cyanophthalane (1-(4'-fluorophenyl)-1,3-dihydroisobenzofuran-5-carbonitrile) with N,N-dimethylaminopropylchloride in a polar aprotic solvent using a strong base.

BACKGROUND OF THE INVENTION

Citalopram and its pharmaceutically acceptable acid addition salts, such as its hydrogen bromide salt (Formula (I)) as described in U.S. Pat. No. 4,136,193, are anti-depressant drugs with few side effects.

Formula (I)

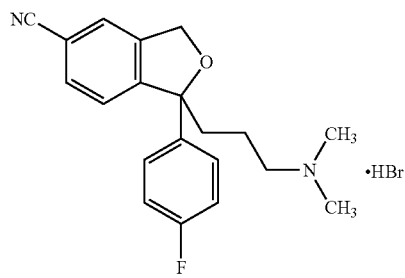

Citalopram hydrobromide

Various processes for the preparation of citalopram have been described in the prior art. For example, U.S. Pat. No. 4,136,193 describes the alkylation of cyanophthalane with 3-dimethylaminopropylchloride, using sodium hydride as a base in a dimethylsulphoxide (DMSO) medium (Scheme-1). The reaction mixture is poured into ice water and extracted with ether. Then, after standard acid-base work-up, crude citalopram base is isolated as an oil. The isolated oil is purified by high vacuum distillation, (0.03 mm at 175-180° C.) and then converted to the hydrobromide salt.

Scheme-1

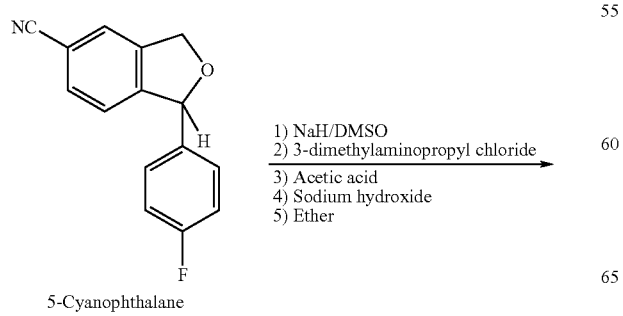

5-Cyanophthalane

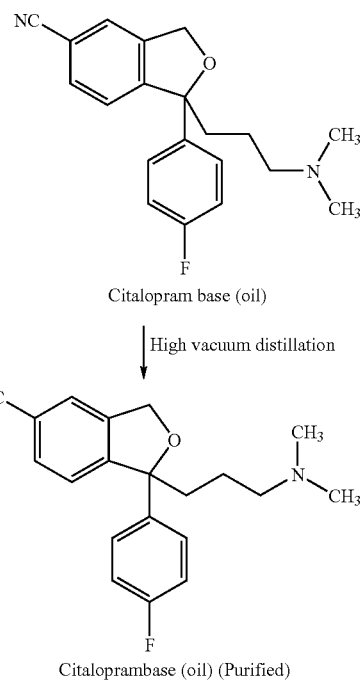

Citalopram base (oil)

High vacuum distillation

Citaloprambase (oil) (Purified)

Another process, as described in WO-A-98/19511, is the alkylation of cyanophthalane with 3-dimethylaminopropylchloride in the presence of a strong base (such as n-butyl lithium) and diisopropylamine in a dimethoxyethane medium at −50° C. (Scheme-2). After completion of the reaction, the reaction mixture is poured into ice water and extracted with toluene. After standard acid-base work-up using toluene as solvent, citalopram base is isolated as an oil. The oily base is then converted to acid addition salts such as citalopram hydrobromide and hydrochloride by conventional methods.

Scheme-2

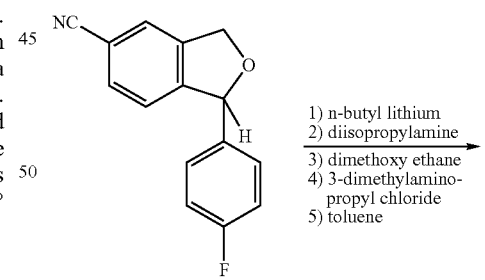

5-Cyanophthalane 1) n-butyl lithium
2) diisopropylamine
3) dimethoxy ethane
4) 3-dimethylamino-propyl chloride
5) toluene

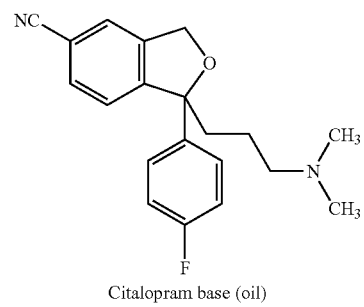

Citalopram base (oil)

A drawback of the above two processes is that the citalopram base is isolated as an oil. Purification of citalopram oily base is carried out by high vacuum distillation (0.03 mm) at 175-181° C. Achieving such a very high vacuum at plant level is difficult and hence the process described is not easily transferable to the commercial scale. Apart from these constraints, citalopram base having a cyano group at the $5^{th}$ position of the bicyclic ring system may decompose during high vacuum distillation at high temperature to form citalopram carboxamide as an impurity, resulting in poor quality and yield.

In yet another process, citalopram is made as described in U.S. Pat. No. 4,650,884. The process involves the successive Grignard reaction of 5-cyanophthalane with 4-fluorophenyl-magnesiumbromide and N,N-dimethylaminopropylmagnesiumchloride and the cyclization of the resulting diol to obtain citalopram base as an oil (Scheme-3). The oily base is converted to the hydrobromide salt using anhydrous hydrogen bromide gas in acetone medium. Due to the poor quality of the oily base, repeated crystallization of the hydrobromide was necessary to obtain a pharmaceutically acceptable quality of citalopram hydrobromide.

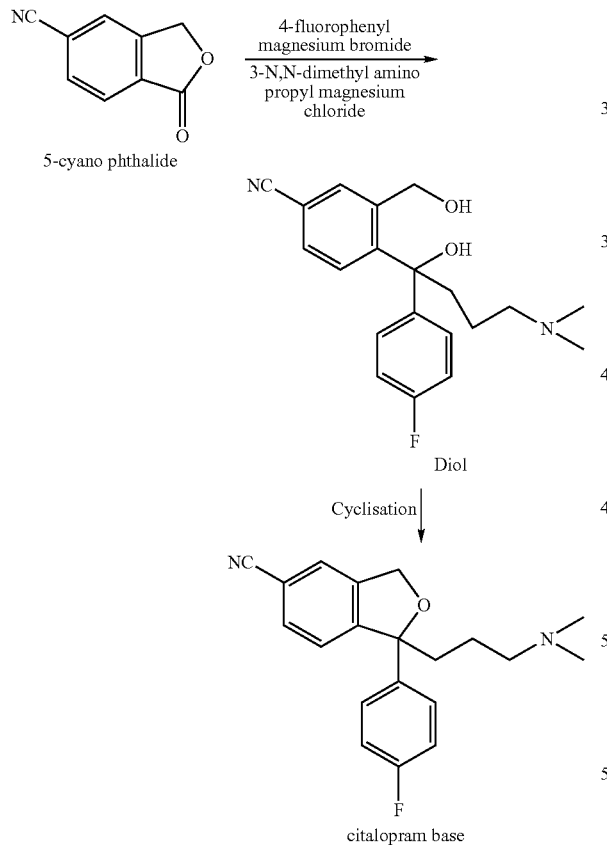

Scheme-3

Using the same strategy, citalopram base may be made as described in CA-A-1,339,452 [equivalent to U.S. Pat. No. 4,943,590, EP-A-347066 & GB-A-8,814,057 Scheme-3]. The racemic diol base, as described in the patent, is dissolved in dichloromethane. Triethylamine and methane sulphonyl chloride are added over a period of 1 hour. The reaction mixture is then washed twice with 0.1M sodium hydroxide solution, the organic phase is separated and dried over anhydrous magnesium sulphate followed by solvent concentration under reduced pressure, and the citalopram base is isolated as a crystalline solid. For the first time, citalopram base has been reported as a crystalline solid. However, no physical data are described here [EP-A-347066]. The solid base is converted to the hydrobromide salt using anhydrous hydrogen bromide gas in acetone medium.

DE-A-20 007 303 discloses yet another process for the isolation of citalopram base, as a solid, from citalopram hydrobromide. However, the process for making citalopram hydrobromide is not described. The isolated crystalline base is then converted into the desired salt. According to the process described here, pure citalopram hydrobromide is dissolved in 5 volumes of water and the pH is adjusted to about 10 with 6N sodium hydroxide. Citalopram base is then extracted into a non-polar organic solvent, such as toluene. The toluene is distilled off under reduced pressure and the resulting residue is triturated with n-heptane to precipitate citalopram base as a solid. The solid is then filtered to produce crystalline citalopram base.

The main disadvantage of this process is that citalopram hydrobromide has to be made first from the crude oily base isolated from the prior art process and then converted back to solid citalopram base. Then, the solid base is again converted to its corresponding hydrobromide salt. Thus, the process involves multiple operations which are tedious and time consuming. In addition, prolonged heating of citalopram base may increase the carboxamide impurity, resulting in poor quality citalopram.

SUMMARY OF THE INVENTION

The present invention provides a process for the isolation of crystalline citalopram base of formula (1) from the alkylation reaction mixture of 1-(4'-fluorophenyl)-1,3-dihydroisobenzofuran-5-carbonitrile (5-cyanophthalane) with N,N-dimethylaminopropylchloride in a polar aprotic solvent medium, such as dimethylsulfoxide (DMSO), in the presence of a strong base, such as potassium tert.-butoxide or sodium hydride, which comprises:

a) diluting the reaction mixture with ice cold water and extracting the resulting mixture with a water-immiscible organic solvent;

b) re-extracting the water-immiscible organic solvent extract with an aqueous acid;

c) diluting the aqueous acid extract with a substantially equal volume of a water miscible organic solvent, based on the volume of water in the aqueous acid extract;

d) adjusting the pH to basic with an inorganic base to precipitate free crystalline base, and e) further isolating the precipitated free crystalline base by filtration.

DETAILED DESCRIPTION OF THE INVENTION

The invention provides a simple and efficient process for the isolation of highly pure crystalline citalopram base directly from the alkylation reaction mixture of 5-cyanophthalane with N,N-dimethylaminopropylchloride in a polar aprotic solvent, preferably DMSO, using a strong base.

According to the present invention, the alkylation of 1-(4-fluorophenyl)-1,3-dihydroisobenzofuran-5-carbonitrile (5-cyanophthalane) with N,N-dimethylaminopropylchloride may be carried out following prior art procedure, and preferably as described in U.S. Pat. No. 4,136,193. However, according to the process described in U.S. Pat. No. 4,136,193, after the completion of the alkylating reaction, the reaction mass is diluted with ice cold water and the aqueous layer is extracted into ether. The ether layer is then extracted with 20% aqueous acetic acid. The pH of the aqueous acidic layer is then adjusted to alkaline, e.g. pH 10-11, with sodium hydroxide and the citalopram base extracted into ether. The ether layer is then concentrated under reduced pressure to obtain citalopram base oil.

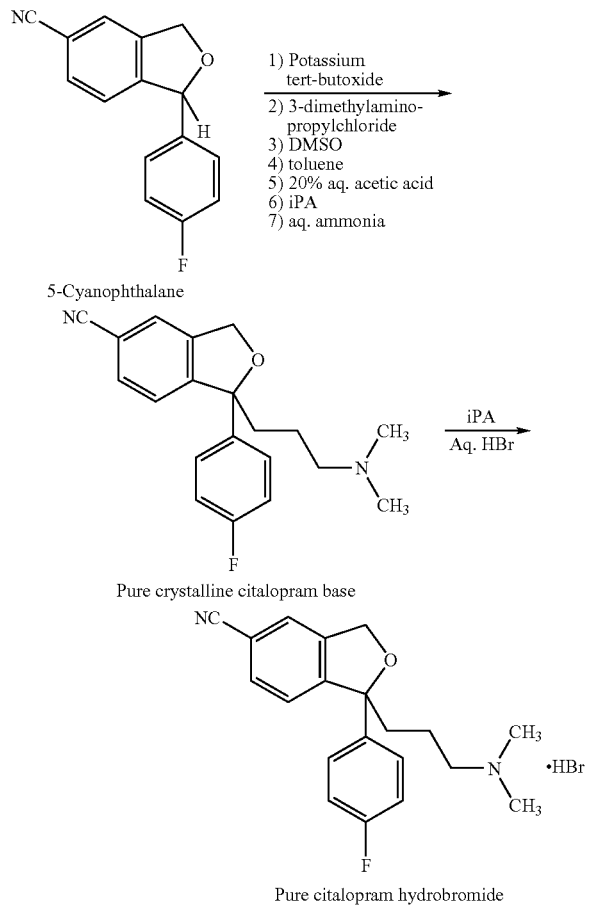

By contrast, according to the present invention (Scheme-4), after the completion of the alkylating reaction, the reaction mass is diluted with ice cold water and extracted with a suitable water immiscible organic solvent, such as toluene, methylenedichloride, chloroform, ethylacetate and diethyl ether, but most preferred is toluene. The toluene layer is then taken for an acid—base work up, as follows.

The acid work-up comprises extracting the organic (preferably, toluene) layer with an aqueous acid, for example a mineral acid such as hydrochloric or hydrobromic acid, or, preferably, a weak organic acid such as formic, oxalic or acetic acid. Most preferred is to use 20% aqueous acetic acid.

To the above aqueous acidic extract, is added a substantially equal volume of a water-miscible solvent, based on the volume of water in the aqueous acid extract. By 'substantially equal' in this context is meant that the water-miscible solvent is added in a ratio (v/v), to water in the aqueous acid extract, in the range from 0.8:1 to 1.2:1, preferably in the range from 0.9:1 to 1.1:1, most preferably 1:1. Suitable water-miscible solvents comprise: alcohols such as methanol, ethanol and isopropanol; ketones such as acetone; dimethylformamide (DMF); and/or dimethylsulphoxide (DMSO), especially isopropylalcohol (IPA)).

Then, the pH of the mixture is carefully adjusted in order to precipitate the crystalline free base. Preferably, the pH is adjusted to about 8.0-9.5, more preferably to about 8.5-9.0, since, at higher pH, impurities start precipitating and, at lower pH, the yield is lower. Suitable bases for adjusting the pH include aqueous ammonia, sodium hydroxide, potassium hydroxide and sodium or potassium carbonates, but preferably a mild base such as aqueous ammonia is used. The precipitation reaction is preferably carried out at below ambient temperature (i.e. below about 25° C.), more preferably between 10-15° C.; at higher temperatures, yield is reduced because of the higher solubility and, at lower temperatures, impurities also precipitate. Preferably, the mixture is then stirred, for example for additional 3-5 hours, to precipitate citalopram completely.

The crystalline citalopram base is then preferably filtered, and preferably also washed with a cold aqueous water-miscible solvent, preferably IPA, and optionally may be washed with a washing agent to remove the water-miscible solvent, such as with a hydrocarbon, e.g. a $C_{5-7}$ alkane or cycloalkane, preferably hexane.

By this method, high purity crystalline citalopram base can be isolated in a single step directly from the alkylation reaction mixture, i.e. the citalopram base can be isolated in crystalline form without prior isolation of crude oily base or crude hydrobromide salt.

The crystalline citalopram base can then be converted to corresponding acid addition salts such as citalopram hydrobromide and citalopram hydrochloride by conventional prior art procedure, preferably using aqueous hydrobromic acid or hydrochloric acid in a alcoholic solvent medium.

The present invention is further illustrated by the following non-limiting examples. In each, the citalopram base was characterized by IR, $^1$H-NMR, HPLC and melting point. Purity was determined by HPLC and found to be in excess of 98%.

EXAMPLES

In the Examples, 1-(4'-fluorophenyl)-1,3-dihydroisobenzofuran-5-carbonitrile (5-cyanophthalane) is prepared by using commercially available 5-bromophthalide as per the process described in U.S. Pat. No. 4,136,193. However, it will be appreciated that commercially available 5-cyanophthalane could instead be used, as per the process described in WO-A-98/19511.

Example 1

Isolation of High Purity Crystalline R,S-Citalopram using Potassium tertiary Butoxide as a Base (a) 72 grams of potassium tertiary butoxide are dissolved in 575 ml of dimethylsulphoxide at 60-70° C. under a nitrogen atmosphere. To the resulting solution of potassium salt of dimethylsulphoxide, 96 g of 1-(4'-fluorophenyl)-1,3-dihydro-isobenzofuran-5-carbonitrile, dissolved in 150 ml of dimethylsulphoxide, is added dropwise over a period of 10 min at 25-30° C. The mixture is then stirred for an additional 10 min at 25-30° C. 53 g of 3-dimethylaminopropylchloride in 25 ml of dimethylsulphoxide are added quickly and the reaction mixture is then heated to 40° C. and maintained for 50 min. The reaction mixture is then poured into ice-water and extracted with toluene. The toluene phase is extracted with 200 ml of 20% aqueous acetic acid (40 ml acetic acid and 160 ml water).

(b) Then, the acetic acid solution is diluted with 160 ml of isopropyl alcohol, cooled to 5-10° C. and the pH is then adjusted to 8.5-9.0 using aqueous ammonia (85 ml) whilst maintaining the temperature between 5-10° C. for 4 hours. The crystalline citalopram base thus produced is then filtered and washed with cold aqueous isopropyl alcohol (20%, 100 ml) followed by washing with 100 ml hexane. The filtrate is dried at 40° C. under a vacuum of 500-600 mm Hg until at constant weight.

Yield: 95-97 g
Purity by HPLC: 99.5%
Highest single impurity: 0.08%
Melting point: 89-91° C.

As shown by the experimental data, a water: isopropyl alcohol ratio of 1:1 has given very good yield and purity of citalopram base.

The details of experimental data with solvents other than isopropyl alcohol/water are given in Table-1

TABLE 1

| Sample No | Solvent | Solvent ratio (v/v) | Yield | Purity by HPLC | Highest single impurity | Melting point (° C.) |
|---|---|---|---|---|---|---|
| 1 | Water, Ethanol | 1:1 | 96 g | 99.25% | 0.15% | 88-90 |
| 2 | Water, Methanol | 1:1 | 95 g | 99.22% | 0.18% | 88-90 |
| 3 | Water, Dimethylformamide | 1:1 | 94 g | 99.12% | 0.24% | 88-90 |
| 4 | Water, Dimethylsulphoxide | 1:1 | 94 g | 98.78% | 0.26% | 87-89 |
| 5 | Water, Acetone | 1:1 | 94 g | 98.94% | 0.16% | 87-89 |

The salient feature of the process of Example 1 is the isolation of high purity crystalline citalopram base directly from the reaction mixture.

Example 2

Isolation of High Purity Crystalline R,S-Citalopram Using Sodium Hydride as a Base.

The procedure of Example 1 is followed, except 72 g of potassium t-butoxide in 575 ml. DMSO is replaced by 21 grams of sodium hydride (60% in mineral oil) dissolved in 900 ml of dimethyl sulphoxide.

Yield: 92-94 g
HPLC purity: 99.32%
Highest single impurity: 0.12%
Melting point: 89-91° C.

The details of experimental data with solvents other than isopropyl alcohol/water are given in the Table-2

TABLE 2

| Sample No | Solvent | Solvent ratio (v/v) | Yield | Purity by HPLC | Highest single impurity | Melting point (° C.) |
|---|---|---|---|---|---|---|
| 1 | Water, Ethanol | 1:1 | 91 g | 99.25% | 0.15% | 88-90 |
| 2 | Water, Methanol | 1:1 | 91 g | 99.22% | 0.17% | 88-90 |

TABLE 2-continued

| Sample No | Solvent | Solvent ratio (v/v) | Yield | Purity by HPLC | Highest single impurity | Melting point (° C.) |
|---|---|---|---|---|---|---|
| 3 | Water, Dimethylformamide | 1:1 | 92 g | 98.32%, | 0.28% | 88-90 |
| 4 | Water, Dimethylsulphoxide | 1:1 | 92 g | 98.78% | 0.26% | 87-89 |
| 5 | Water, Acetone | 1:1 | 90 g | 98.84% | 0.18% | 87-89 |

The above data show improved yield and purity over corresponding prior art processes.

The invention claimed is:

1. A process for the isolation of crystalline citalopram base of formula (1)

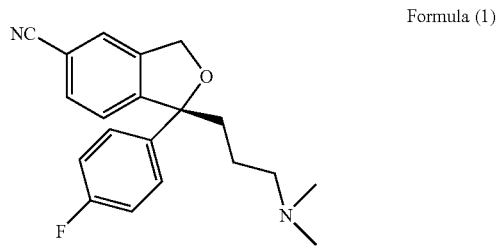

Formula (1)

from the alkylation reaction mixture of 1-(4'-fluorophenyl)-1,3-dihydroisobenzofuran-5-carbonitrile (cyanophthalane) of formula (2)

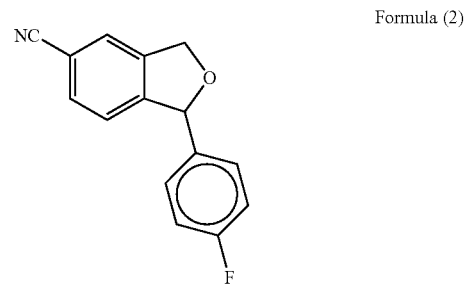

Formula (2)

with N,N-dimethylaminopropylchloride in a polar aprotic solvent medium in the presence of a strong base, which comprises:
   a) diluting the reaction mixture with ice cold water and extracting the resulting mixture with a water-immiscible organic solvent;
   b) re-extracting the water-immiscible organic solvent extract with an aqueous acid;
   c) diluting the aqueous acid extract with a substantially equal volume of a water miscible organic solvent, based on the volume of water in the aqueous acid extract;
   d) adjusting the pH to basic with an inorganic base to precipitate free crystalline base, and
   e) further isolating the precipitated free crystalline base by filtration.

2. A process according to claim 1, wherein the water-immiscible organic solvent is selected from methylenedichloride (MDC), chloroform (CHCl$_3$), toluene, diethyl ether, ethyl acetate, and mixtures thereof.

3. A process according to claim 2, wherein the water-immiscible organic solvent is toluene.

4. A process according to claim 1, wherein the aqueous acid is a mineral acid selected from hydrochloric acid and hydrobromic acid, or a weak organic acid selected from formic acid, acetic acid and oxalic acid, or a mixture thereof.

5. A process according to claim 4, wherein the aqueous acid is acetic acid.

6. A process according to claim 5, wherein the acetic acid is 20% v/v in water.

7. A process according to claim 1, wherein the water miscible organic solvent is selected from methanol, ethanol, isopropyl alcohol, acetone, acetonitrile, dimethylformamide (DMF) and dimethylsulphoxide (DMSO), and mixtures thereof.

8. A process according to claim 7, wherein the water miscible organic solvent is isopropyl alcohol.

9. A process according to claim 1, wherein the inorganic base is selected from sodium carbonate or hydroxide, potassium carbonate or hydroxide, and liquor ammonia.

10. A process according to claim 1, wherein the inorganic base is liquor ammonia.

11. A process according to claim 1, wherein the pH is adjusted to 8.0-9.5.

12. A process according to claim 1, wherein the pH is adjusted to 8.5-9.0 at temperature between 10-15° C.

13. A process according to claim 1, further comprising (f) washing the isolated free crystalline base with cold aqueous isopropyl alcohol.

14. A process according to claim 13, further comprising (g) washing the isolated free crystalline base with hexane to remove the isopropyl alcohol.

15. A process according to claim 13 or claim 14, further comprising (h) drying the washed isolated free crystalline base.

* * * * *